United States Patent
Peng et al.

(10) Patent No.: US 9,466,105 B2
(45) Date of Patent: Oct. 11, 2016

(54) MAGNETIC RESONANCE IMAGING WHITE MATTER HYPERINTENSITIES REGION RECOGNIZING METHOD AND SYSTEM

(71) Applicants: National Central University, Taoyuan (TW); Huan-Cheng Chang, Taoyuan (TW)

(72) Inventors: Syu-Jyun Peng, Hsinchu County (TW); Yu-Wei Chen, Taoyuan (TW); Jang-Zern Tsai, Taoyuan (TW); Kuo-Wei Wang, Taoyuan (TW)

(73) Assignees: National Central University, Taoyuan (TW); Huan-Cheng Chang, Taoyuan (TW)

( * ) Notice: Subject to any disclaimer, the term of this patent is extended or adjusted under 35 U.S.C. 154(b) by 0 days.

(21) Appl. No.: 14/715,565

(22) Filed: May 18, 2015

(65) Prior Publication Data
US 2016/0196644 A1 Jul. 7, 2016

(30) Foreign Application Priority Data
Jan. 5, 2015 (TW) .............................. 104100102 A (51) Int. Cl.
*G06K 9/00* (2006.01)
*G06T 7/00* (2006.01)
*G01R 33/563* (2006.01)
(Continued)

(52) U.S. Cl.
CPC ......... *G06T 7/0012* (2013.01); *G01R 33/5602* (2013.01); *G01R 33/5608* (2013.01); *G01R 33/56341* (2013.01); *G06T 7/0081* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 6,430,430 B1 * 8/2002 Gosche .................. G06T 7/0012
128/920
7,634,302 B2 * 12/2009 Gupta ................. G01R 33/4824
324/307

(Continued)

FOREIGN PATENT DOCUMENTS

| CN | 101496723 B | 10/2010 |
|----|-------------|---------|
| TW | 200903008 A | 1/2009 |
| WO | 0065985 A2 | 11/2000 |

OTHER PUBLICATIONS

Shi et al ("Automated Quantification of white matter lesion in magnetic resonance imaging of patients with acute infarctions", 2013.*

(Continued)

*Primary Examiner* — Avinash Yentrapati
(74) *Attorney, Agent, or Firm* — CKC & Partners Co., Ltd.

(57) ABSTRACT

A magnetic resonance imaging white matter hyperintensities region recognizing method and system are disclosed herein. The white matter hyperintensities region recognizing method includes receiving and storing a FLAIR MRI image, a spin-lattice relaxation time weighted MRI image, and a diffusion weighted MRI image. Registration and fusion are preformed, and a white matter mask is determined. An intersection image of the FLAIR MRI image and the white matter mask is taken, a first region is determined after normalizing the intersection image, a cerebral infarct region is removed from the first image through the diffusion weighted MRI image, and then a determination is made as to whether to remove a remaining region in order to form a white matter hyperintensities region in the FLAIR MRI image.

12 Claims, 8 Drawing Sheets

(51) Int. Cl.
*G01R 33/56* (2006.01)
*A61B 5/055* (2006.01)
*A61B 5/00* (2006.01)

(52) U.S. Cl.
CPC .............. *G06T 2207/10088* (2013.01); *G06T 2207/30016* (2013.01)

(56) References Cited

U.S. PATENT DOCUMENTS

| 7,995,825 B2* | 8/2011 | Jack | A61B 5/055 382/128 |
|---|---|---|---|
| 2003/0009098 A1* | 1/2003 | Jack | A61B 5/055 600/410 |

OTHER PUBLICATIONS

Tsai et al ("Automated Segmentation and Quantification of White Matter Hyperintensities in Acute Ischemic Stroke Patients with Cerebral Infarction", Aug. 2014).*

Jang-Zern Tsai et al. "Automated Segmentation and Quantification of White Matter Hyperintensities in Acute Ischemic Stroke Patients with Cerebral Infarction", PLOS One, Aug. 2014, vol. 9, Issue 8, e104011, Published Aug. 15, 2014.

Petronella Anbeek et al., "Probabilistic segmentation of white matter lesions in MR imaging", Neuroimage 21(2004) 1037-1044, accepted Oct. 8, 2003.

Petronella Anbeek et al., "Automatic segmentation of different-sized white matter lesions by voxel probability estimation", Medical Image Analysis 8(2004), 205-215, Available online Aug. 4, 2004.

Petronella Anbeek et al., "Probabilistic segmentation of brain tissue in MR imaging", NeuroImage 27(2005) 795-804, Available online Jul. 12, 2005.

Richard Beare et al., "Development and validation of morphological segmentation of age-related cerebral white matter hyperintensities" NeuroImage 47(2009) 199-203, Available online Apr. 1, 2009.

Stefan Kloppel et al., "A comparison of different automated methods for the detection of white matter lesions in MRI data", NeuroImage 57(2011) 416-422, Available online May 3, 2011.

Lin Shi et al., "Automated quantification of white matter lesion in magnetic resonance imaging of patients with acute infarction", Journal of Neuroscience Methods 213(2013) 138-146, Accepted Dec. 14, 2012.

A thesis "Development of Automatic Detection Methods for Exploration of Lesional and Non-lesional Neurological Disorders with Magnetic Resonance Imaging", submitted by Syu-Jyun Peng to the National Central University, NCU Institutional Repository, pp. 37-51, Jun. 2014.

* cited by examiner

MAGNETIC RESONANCE IMAGING WHITE MATTER HYPERINTENSITIES REGION RECOGNIZING METHOD AND SYSTEM

RELATED APPLICATIONS

This application claims priority to Taiwanese Application Serial Number 104100102, filed Jan. 5, 2015, which is herein incorporated by reference.

BACKGROUND

1. Field of Invention

The present invention relates to image recognizing technology. More particularly, the present invention relates to a magnetic resonance imaging white matter hyperintensities region recognizing method and system.

2. Description of Related Art

In the prior art, because a white matter hyperintensities (WMH) region is distinctive compared with a general white matter region in a fluid-attenuated inversion recovery (FLAIR) magnetic resonance imaging (MRI) image, such as FLAIR image is often used as a method to distinguish a WMH region from the general white matter region. However, a cerebral infarct region has a voxel intensity that is similar to the voxel intensity of a general white matter region so that it is difficult to clearly distinguish a WMH region from a cerebral infarct region, easily leading to confusion if simply a FLAIR MRI image is utilized. Recognition becomes even more difficult when the two regions overlap.

SUMMARY

In order to recognize a WMH region and a cerebral infarct region in an MRI image, an aspect of the present disclosure provides an MRI white matter hyperintensities region recognizing method including a number of steps. In the white matter hyperintensities region recognizing method, (a) a fluid attenuation inversion recovery (FLAIR) MRI image, a spin-lattice relaxation time (defined as T1) weighted MRI image and a diffusion weighted MRI image are received. (b) The FLAIR MRI image, the T1 weighted MRI image and the diffusion weighted MRI image are stored. (c) With respect to the FLAIR MRI image, the T1 weighted MRI image and the diffusion weighted MRI image are registered to form a registered T1 weighted MRI image and a registered diffusion weighted MRI image. (d) The FLAIR MRI image and the registered T1 weighted MRI image are fused to form a fused image, and a white matter mask is determined through the fused image. (e) An intersection image of the FLAIR MRI image and the white matter mask is taken. (f) The intersection image is normalized. (g) After step (f), when an intensity value of a voxel in the intersection image is larger than a voxel intensity threshold value, the voxel is selected as belonging to a first region. (h) A second region is determined through the registered diffusion weighted MRI image. (i) When a continuous area of the first region overlaps the second region, the second region is removed from the continuous area to form a remaining region. (j) When the continuous area overlaps the second region and a ratio of the second region to the continuous area is larger than a predetermined value, the remaining region is removed.

In an embodiment of the present disclosure, a junction region of cerebral gray matter and white matter is determined from the fused image. Before removing the second region, the junction region is removed from the first region.

In an embodiment of the present disclosure, a set of transformation parameters is determined from the fused image and a known template brain image by diffeomorphic anatomical registration through exponentiated Lie algebra (DARTEL), wherein the set of transformation parameters is used for mutual deformation of the fused image and the known template brain image.

In an embodiment of the present disclosure, a binarization process of a known template white matter image is executed to form a template white matter mask. A deformation process of the template white matter mask is executed through the set of transformation parameters to form an initial white matter mask.

In an embodiment of the present disclosure, a template corpus callosum mask is determined from the known template brain image. A deformation process of the template corpus callosum mask is executed through the set of transformation parameters to form a corpus callosum mask.

In an embodiment of the present disclosure, an intersection process of the initial white matter mask and the corpus callosum mask is executed to form the white matter mask.

Another aspect of the present disclosure provides an MRI white matter hyperintensities region recognizing system. The white matter hyperintensities region recognizing system includes an input device, a storage device and a processor. The input device receives a FLAIR MRI image, a T1 weighted MRI image and a diffusion weighted MRI image. The storage device stores the FLAIR MRI image, the T1 weighted MRI image and the diffusion weighted MRI image. The processor is coupled to the storage device and executes a number of steps. (a) With respect to the FLAIR MRI image, the T1 weighted MRI image and the diffusion weighted MRI image are registered to form a registered T1 weighted MRI image and a registered diffusion weighted MRI image. (b) The FLAIR MRI image and the registered T1 weighted MRI image are fused to form a fused image, and a white matter mask is determined through the fused image. (c) An intersection image of the FLAIR MRI image and the white matter mask is taken. (d) The intersection image is normalized. (e) After step (d), when an intensity value of a voxel in the intersection image is larger than a voxel intensity threshold value, the voxel is selected as belonging to a first region. (f) A second region is determined through the registered diffusion weighted MRI image. (g) When a continuous area of the first region overlaps the second region, the second region is removed from the continuous area to form a remaining region. (h) When the continuous area overlaps the second region and a ratio of the second region to the continuous area is larger than a predetermined value, the remaining region is removed.

In an embodiment of the present disclosure, the processor determines a junction region of cerebral gray matter and white matter from the fused image, and removes the junction region from the first region before removing the second region.

In an embodiment of the present disclosure, the processor determines a set of transformation parameters from the fused image and a known template brain image by DARTEL, and the set of transformation parameters is used for mutual deformation of the fused image and the known template brain image.

In an embodiment of the present disclosure, the processor executes a binarization process of a known template white matter image to form a template white matter mask, and executes a deformation process of the template white matter mask through the set of transformation parameters to form an initial white matter mask.

In an embodiment of the present disclosure, the processor determines a template corpus callosum mask from the known template brain image, and executes a deformation process of the template corpus callosum mask through the set of transformation parameters to form a corpus callosum mask.

In an embodiment of the present disclosure, the processor executes an intersection process of the initial white matter mask and the corpus callosum mask to form the white matter mask.

In sum, the present disclosure is directed to recognizing a WMH region and a cerebral infarct region in an MRI image through removing a cerebral infarct region with the assistance of a diffusion weighted MRI image and reserving a WMH region of a FLAIR MRI image by determining whether a remaining region is peri-infarct edema through the aforementioned embodiments. Moreover, the WMH region is automatically detected to eliminate the burden associated with manual recognition, build a consistent standard, and improve the recognizing efficiency.

The following is a detailed description of the aforementioned contents through embodiments, and provides further explanation of the technical aspects of the present disclosure.

BRIEF DESCRIPTION OF THE DRAWINGS

In order to make the aforementioned contents, and other purposes, features, advantages, and embodiments more clear and understandable, with description made to the accompanying drawings as follows.

DETAILED DESCRIPTION

Reference will now be made in detail to embodiments of the present disclosure, examples of which are described herein and illustrated in the accompanying drawings. While the disclosure will be described in conjunction with embodiments, it will be understood that they are not intended to limit the invention to these embodiments. On the contrary, the invention is intended to cover alternatives, modifications and equivalents, which may be included within the spirit and scope of the disclosure as defined by the appended claims.

Figure 1A:
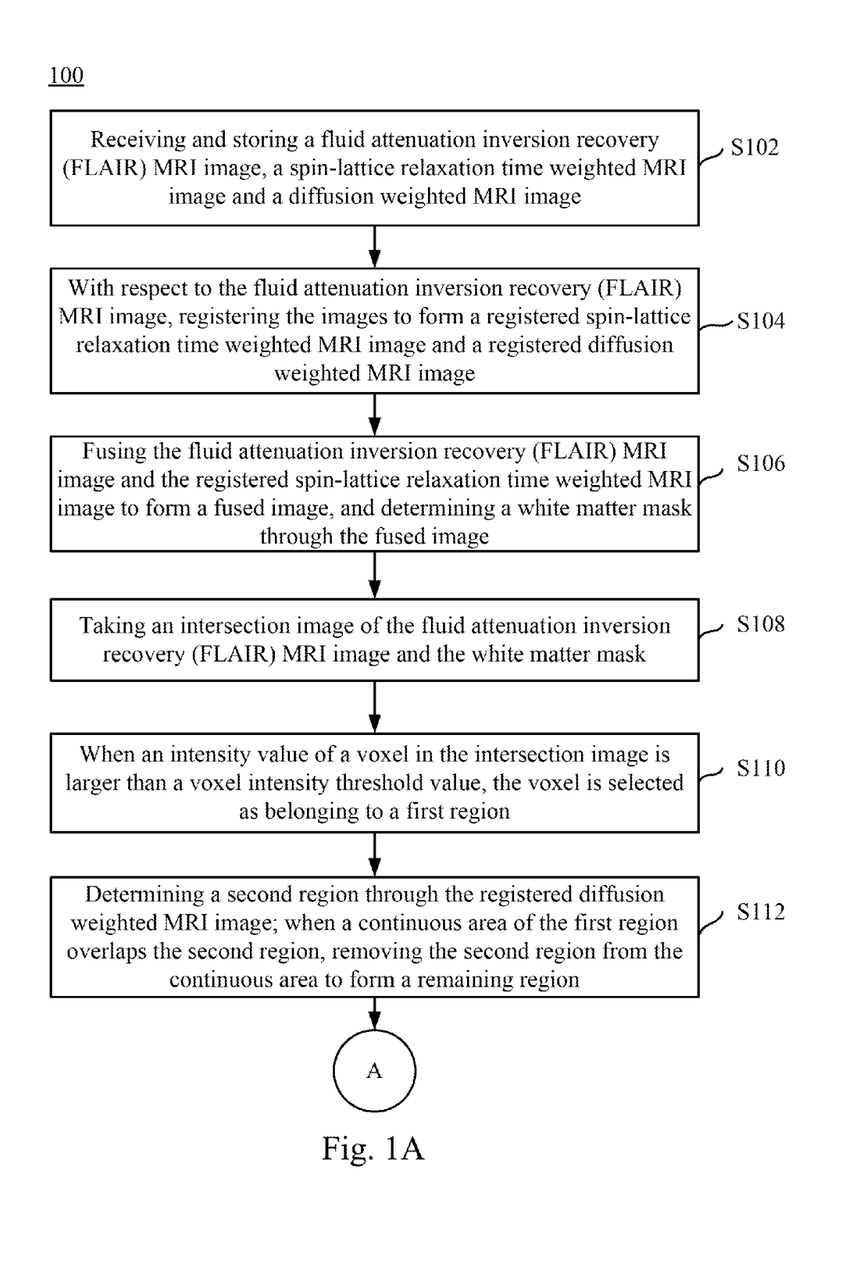
FIGS. 1A and 1B are flow charts of a magnetic resonance imaging white matter hyperintensities region recognizing method according to an embodiment of the present disclosure.
Figure 1B:
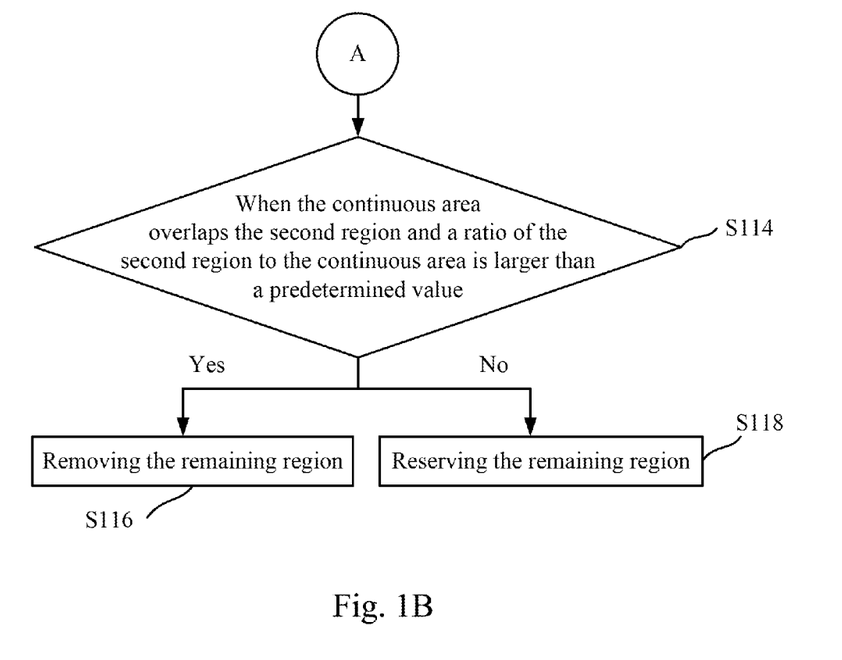

FIGS. 1A and 1B show flow charts of a magnetic resonance imaging (MRI) white matter hyperintensities region recognizing method according to an embodiment of the present disclosure, where point A is a connection point of the steps in FIGS. 1A and 1B. The MRI white matter hyperintensities region recognizing method 100 includes a plurality of steps S102-S118. However, those skilled in the art should understand that the sequence of the steps in the present embodiment can be adjusted according to actual needs, unless such a sequence is specified. All or some of the steps can even be executed simultaneously.

First, in step S102, a fluid attenuation inversion recovery (FLAIR) MRI image, a spin-lattice relaxation time (defined as T1) weighted MRI image and a diffusion weighted MRI image are received as sources for image processing. The FLAIR MRI image, the T1 weighted MRI image and the diffusion weighted MRI image are stored for subsequent image processing. Although the FLAIR MRI image, the T1 weighted MRI image and the diffusion weighted MRI image are usually measured when a target object is immobilized, some external factors (e.g., head movement of the target object) that cause slight movement of the image are still difficult to avoid, and therefore in step S104, the images are registered. With respect to the FLAIR MRI image, locations of the spin-lattice relaxation time weighted MRI image and locations of the diffusion weighted MRI image are adjusted so that voxels of the three images have a location corresponding to the relation of brain structure for the subsequent image processing. After the image registration, a registered T1 weighted MRI image and a registered diffusion weighted MRI image are formed.

If the target object has WMH in a FLAIR image, the voxel intensity of the same location is lower in a T1 weighted MRI image so that this is often mistaken to be gray matter. Therefore, in step S106, the registered T1 weighted MRI image $V_{registered\ T1w}$ is compensated by the FLAIR image $V_{FLAIR}$, and the two images are fused to form a fused image by the following equation of voxel intensity:

$$V_{fusion}=kV_{registered\ T1w}+(1-k)V_{FLAIR}$$

Where k is a constant and its range is [0, 1]. In the present embodiment, k is set as 0.8 and the fused image can be used to distinguish gray matter regions from white matter regions. A white matter mask is then determined through the fused image to emphasize the white matter region in the image.

Figure 2A:
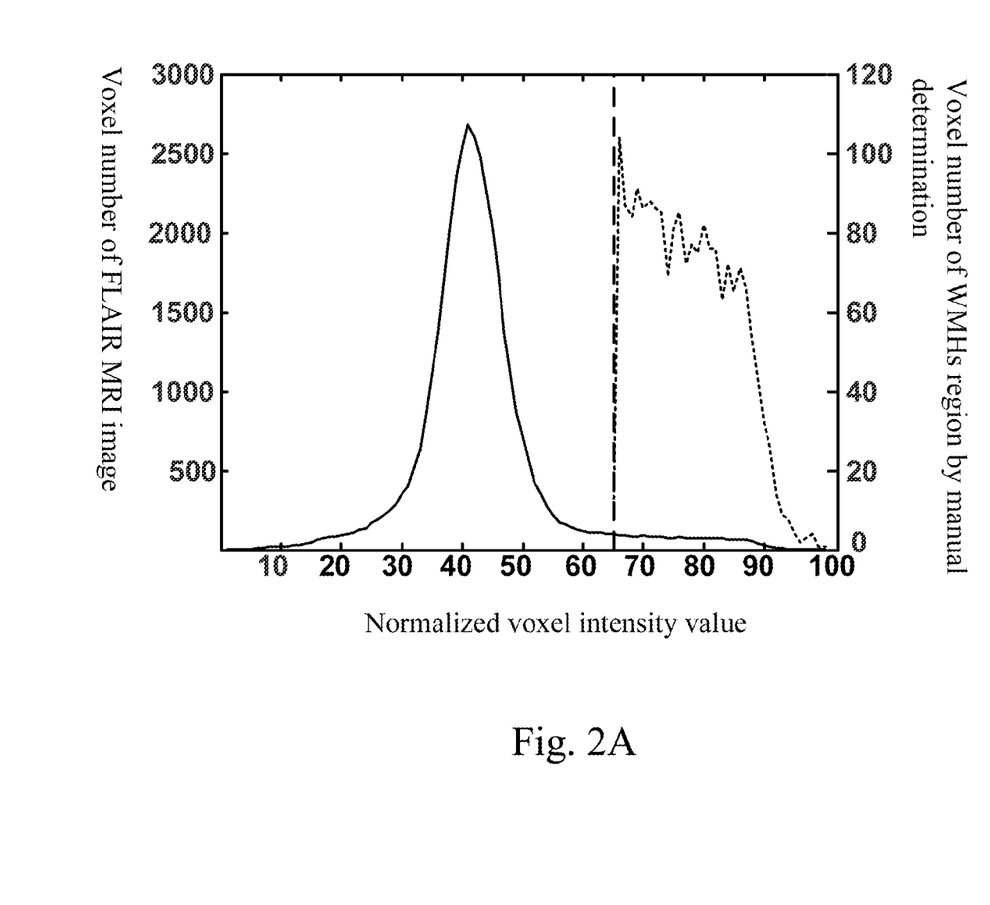
FIGS. 2A and 2B are voxel intensity distribution diagrams of FLAIR MRI images.
Figure 2B:
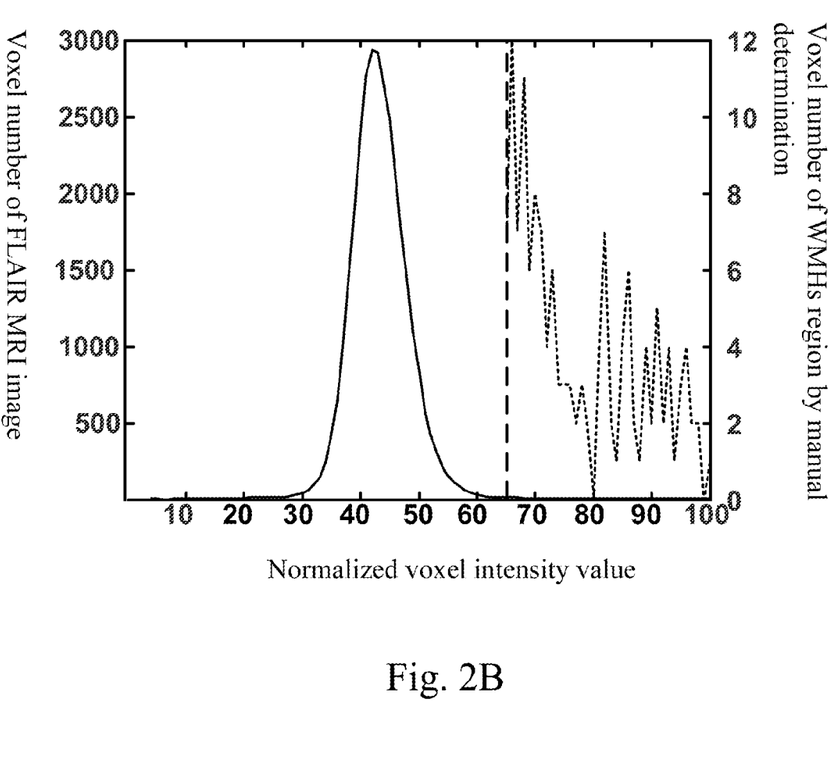

In step S108, in order to exclude regions except for white matter regions to execute a WMH region analysis process, an intersection image is formed by taking an intersection of the aforementioned white matter mask and the FLAIR MRI image. In other words, intensity values of voxels in the white matter mask and location-corresponding intensity values of voxels in the FLAIR MRI image are multiplied together, and the resulting product shows that intensity values of voxels in the other regions are all zeros except for the white matter region so that the other regions displayed black, and the white matter region remains in the FLAIR MRI image. In addition, because the voxel intensity distributed range of every FLAIR MRI image pending for analysis is not necessarily the same, intensity values of voxels in the intersection image undergo a normalization process so that ranges of the values are all adjusted to [0, 100] for application as WMH determining conditions before the WMH region is determined. In step S110, the intensity values of the voxels are inspected in turn, and if an intensity value of a voxel is larger than a voxel intensity threshold value, then the voxel is selected as belonging to a first region indicating that it may be a WMH region. In the present embodiment, the voxel intensity threshold value is set as 65, and if an intensity value of a voxel is larger than 65, then the voxel is selected as belonging to a first region indicating that it may be a WMH region. The voxel intensity threshold value also can be flexibly designed according to actual requirements. Specifically, in FIG. 2A, a WMH region of a target object right hemisphere brain has a volume of 7.954 ml in a FLAIR MRI image, a vertical dashed line indicates the voxel intensity threshold value 65, a dotted line indicates a manually determined WMH region, and a solid line indicates distribution of all voxel intensity, in which intensity values of voxels larger than 65 are selected as belonging to the first region. In FIG. 2B, a WMH region of another target object right hemisphere brain has a volume of 0.736 ml in a FLAIR MRI image, a vertical dashed line indicates the voxel intensity threshold value 65, a dotted line indicates a manually determined WMH region, and a solid line indicates distribution of all voxel intensity, in which intensity values of voxels larger than 65 are selected as belonging to the first region. From FIGS. 2A and 2B, it can be understood that when a target object has a WMH region with a small volume, the variation range of voxel numbers in a manually determined WMH region is large and it is difficult to confirm whether there is a voxel with a value larger than 65 that is not selected as belonging to the first region. However, the present disclosure performs a determination with respect to all intensity values of voxels that can check all voxels in the image and has a higher efficiency compared to the manually determined method.

Figure 3A:
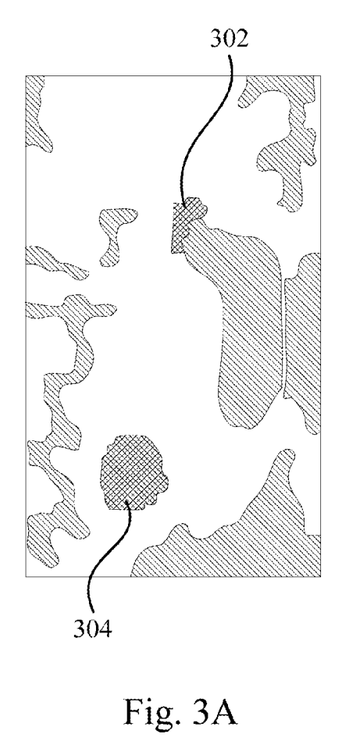
FIG. 3A is a schematic FLAIR MRI image with marked first regions.

Because the voxel intensity of a cerebral infarct region is close to the voxel intensity of a WMH region in a FLAIR MRI image, the cerebral infarct region is usually selected as belonging to the first region in step S110. As shown in FIG. 3A, a WMH region 302, a cerebral infarct region and a surrounding region thereof are all selected as belonging to the first region in step S110, and the aforementioned registered diffusion weighted MRI image is used to distinguish the three regions.

Figure 3B:
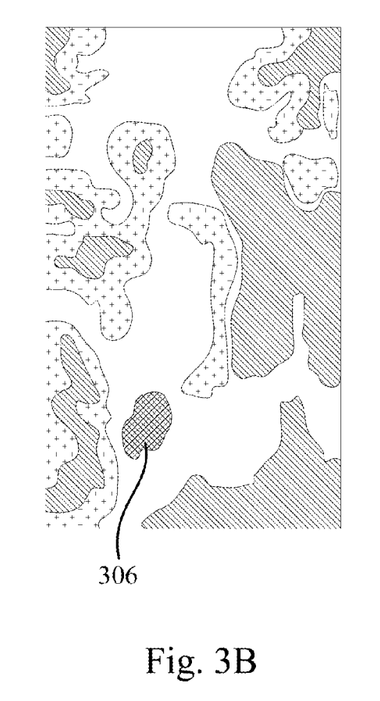
FIG. 3B is a schematic diffusion weighted MRI image with a marked second region.
Figure 3C:
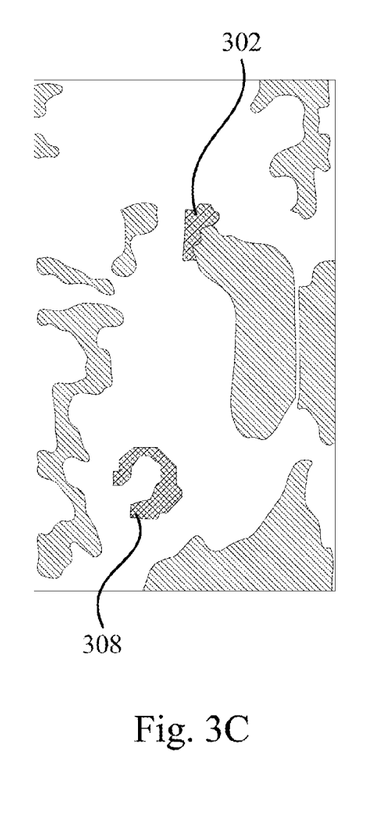
FIG. 3C is a schematic FLAIR MRI image with the marked first regions after removing the second region.
Figure 3D:
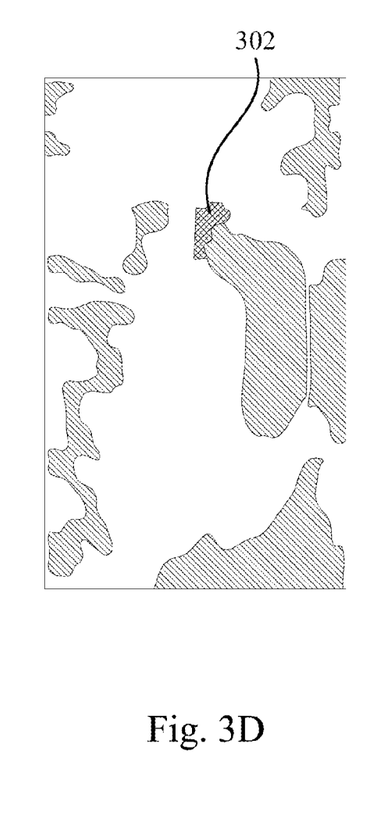
FIG. 3D is a schematic FLAIR MRI image with the marked first regions after removing the second region and a remaining region.

In step S112, as shown in FIG. 3B, the cerebral infarct region is distinctive in the registered diffusion weighted MRI image, and therefore the cerebral infarct region can be marked through the registered diffusion weighted MRI image to form a second region 306. When a continuous area 304 of the first region overlaps the second region 306, the second region 306 is removed from the continuous area 304 to form a remaining region 308 (FIG. 3C), in which the cerebral infarct region and the surrounding region thereof that overlaps the second region 306 are the aforementioned continuous area 304. In addition, a surrounding edema phenomenon often accompanies the cerebral infarct region and may lie in a circular region that is peripheral to the second region 306 and not included in the second region 306 so that the edema region is not removed when the second region 306 is removed from the continuous area 304 to form a remaining region 308. In steps S114-118, a voxel number ratio of the second region to the continuous area is a condition of determining the edema region. When the continuous area 304 overlaps the second region 306 and a voxel number ratio of the second region 306 to the continuous area 304 is larger than a predetermined value, then the remaining region 308 is determined as a peri-infarct edema of cerebral infarct and the remaining region 308 is removed (step S116). The remaining region 308 is reserved if it does not satisfy the condition. Specifically, the predetermined value is 80%, the continuous area 304 that overlaps the second region 306 is the cerebral infarct region and the surrounding region thereof, and when a voxel intensity ratio of the second region 306 to the continuous area 304 is larger than 80%, then the remaining region is removed to form a FLAIR MRI image with only the WMH region 302 marked (FIG. 3D). If there is at least one continuous area 304 that overlaps the second region 306, an independent determination is made as to whether at least one remaining region 308 after removing the second region 306 is to be removed or reserved by each voxel number ratio. The present disclosure not only removes the cerebral infarct region with similar voxel intensity, but also has a mechanism of removing the surrounding region of the cerebral infarct region so that an image with the WMH region is generated after the two filtering steps through the present embodiment of the present disclosure.

Figure 4A:
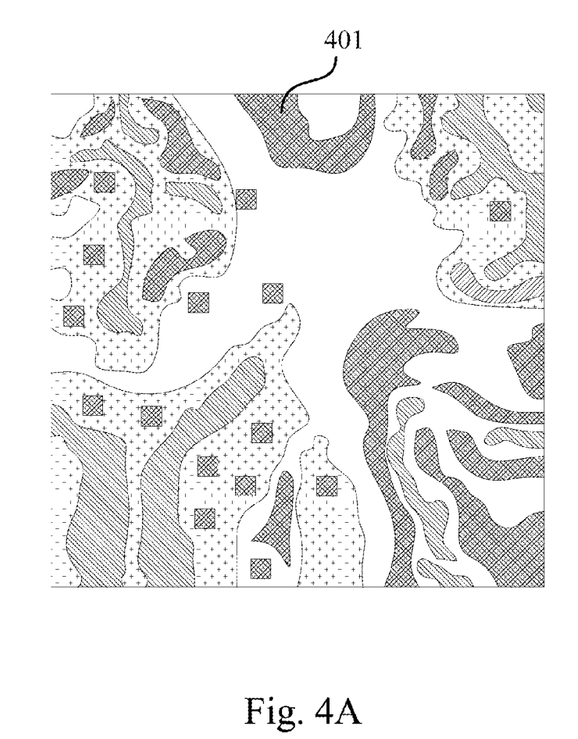
FIG. 4A is a schematic FLAIR MRI image with marked junction regions of cerebral gray matter and white matter.
Figure 4B:
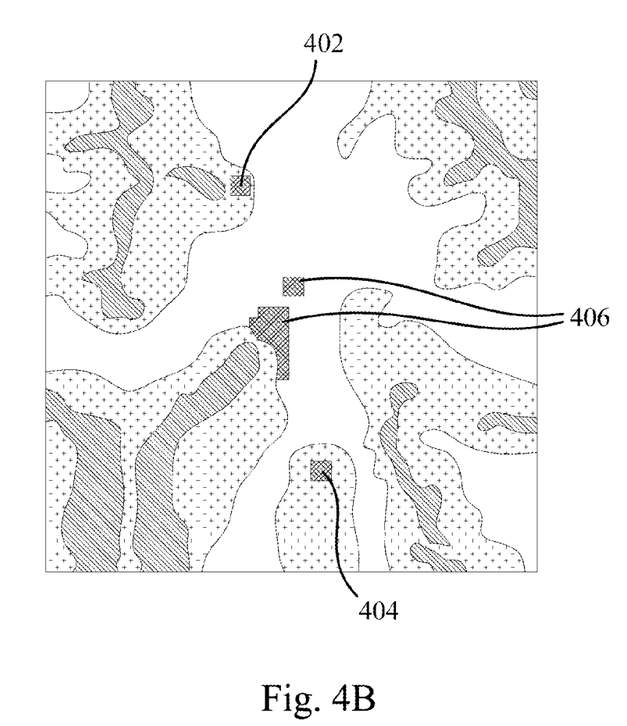
FIG. 4B is a schematic FLAIR MRI image with marked first regions.

However, voxel intensity of a junction region of cerebral gray matter and white matter is also close to voxel intensity of a WMH region in a FLAIR MRI image so that the junction region may be selected as belonging to the first region, and therefore the junction region of cerebral gray matter and white matter must be removed from the first region. In one embodiment, step S118 includes a process of determining a junction region of cerebral gray matter and white matter from the fused image. If an intensity value of a voxel is between $(I_{average,\ GM}+0.5I_{stdev,\ GM})$ and $(I_{average,\ WM}-0.5I_{stdev,\ WM})$, then the voxel is determined as the junction region 401 of cerebral gray matter and white matter, as shown as the mesh region in FIG. 4A, where $I_{average,\ GM}$ is an average value of voxel intensity in the gray matter region, $I_{stdev,\ GM}$ is a standard deviation of voxel intensity in the gray matter region, $I_{average,\ WM}$ is an average value of voxel intensity in the white matter region, and $I_{stdev,\ WM}$ is a standard deviation of voxel intensity in the white matter region. Before the second region is removed, the junction region 401 is removed from the first region. This is realized by performing a method involving determining that a central voxel is junction-connected if a central voxel or any of the eight neighboring voxels thereof in the first region overlaps the aforementioned junction region 401 of cerebral gray matter and white matter. As shown in FIG. 4B, if over 80% of voxels in a continuous area are junction-connected, then the continuous area is determined to be junction-connected and removed from the first region to exclude the junction regions 402, 404 of cerebral gray matter and white matter and reserve the first region 406 without the junction region of cerebral gray matter and white matter.

In order to generate a white matter mask suitable for a target object, in one embodiment, step S108 includes a process of determining a set of transformation parameters through DARTEL, in which the set of transformation parameters is used for mutual deformation of an ICBM (International Consortium for Brain Mapping) template image and the fused image of the target object. A white matter image and a gray matter image are separately selected from the ICBM template image, and a white matter image and a gray matter image are also separately selected from the fused image. The four images are analyzed to generate the set of transformation parameters through a DARTEL module embedded in SPM8 (Statistical Parametric Mapping 8) software. By using the set of transformation parameters, template images are inputted as images of a target object, and after a deformation process, images that anatomically correspond to the template images are outputted.

In one embodiment, step S108 includes a binarization process of a template white matter image to form a template white matter mask, in which intensity values of voxels are all in the range of [0, 1] and a condition of the binarization process is set such that when an intensity value of a voxel is larger than 0.5, the voxel is determined as the white matter region and the intensity value of the voxel is designated as one. If an intensity value of a voxel is smaller than 0.5, the intensity value of the voxel is designated as zero. Therefore, the template white matter mask is formed, and subsequently, the template white matter mask is deformed into an initial white matter mask of the target object, in which the initial white matter mask anatomically corresponds to the template white matter mask through the aforementioned set of transformation parameters generated by DARTEL.

However, because the voxel intensity of a corpus callosum region of the brain is close to the voxel intensity of a white matter region in a FLAIR MRI image, intensity values of voxels in the corpus callosum region are also designated as one in the aforementioned binarization process, and therefore, the corpus callosum region must be removed from the initial white matter mask to form a white matter mask without the corpus callosum region. In one embodiment, step S108 includes a process of determining a template corpus callosum mask from the ICBM template image, and the template corpus callosum mask is deformed into a corpus callosum mask of the target object through the aforementioned set of transformation parameters generated by DARTEL. In one embodiment, an intersection process of the initial white matter mask and the corpus callosum mask is executed. In other words, the intensity values of the voxels in the two masks that are located correspondingly are multiplied together to form the white matter mask without the corpus callosum region. In an alternative embodiment, the aforementioned corpus callosum mask is formed by manually determining a corpus callosum region and designating intensity values of the voxels in the corpus callosum region as zeros.

In an alternative embodiment, the disclosed white matter hyperintensities region recognizing method 100 can also be implemented as a computer program, in which the operation processes of the computer program are as mentioned above and will not repeated hereinafter. The implemented computer program can be stored in a non-transitory computer-readable storage medium, which is loaded by a computer to make the computer execute the white matter hyperintensities region recognizing method 100. The non-transitory computer-readable medium may be a read-only memory (ROM), a flash memory, a floppy disk, a hard disk, an optical disk, a pen drive, a magnetic tape, a network accessible database, or any other suitable non-transitory computer-readable medium with the same function.

Figure 5:
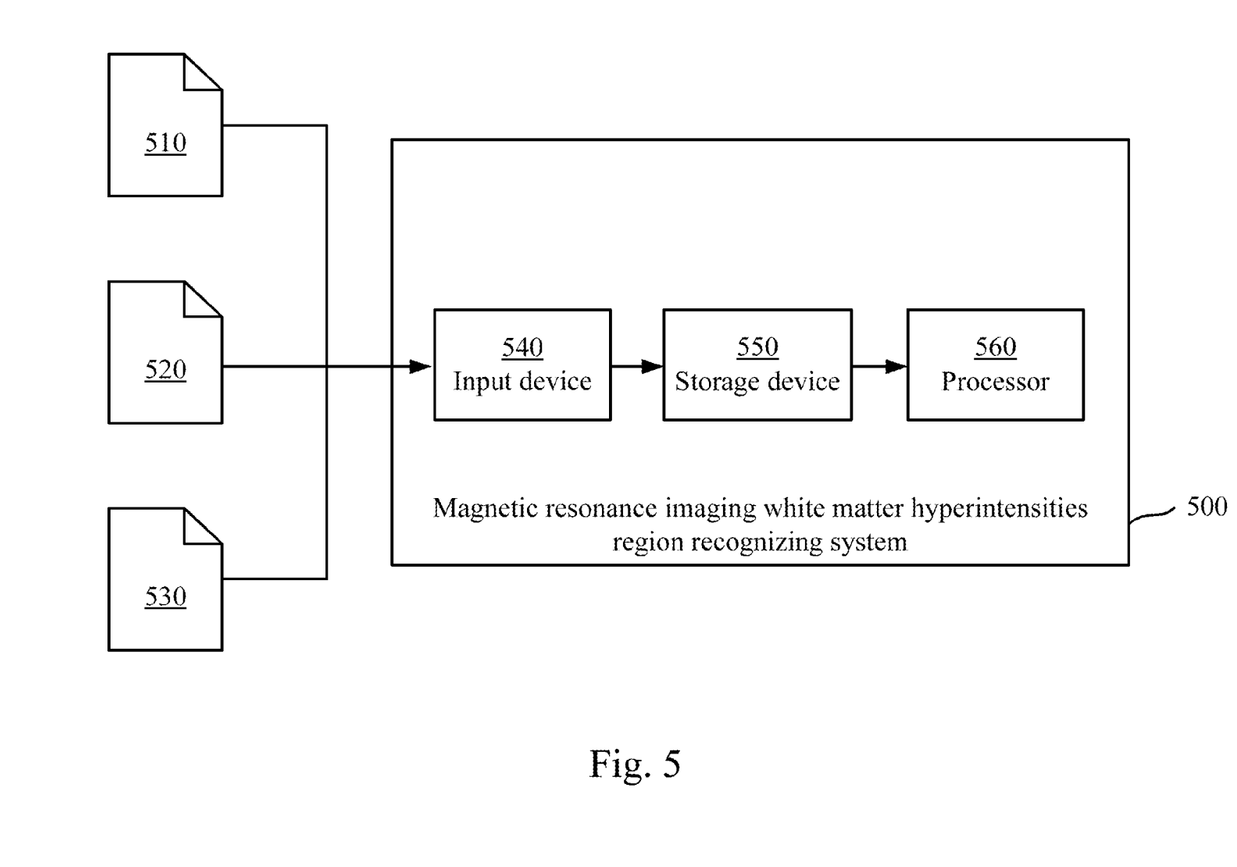
FIG. 5 is a schematic diagram of a magnetic resonance imaging white matter hyperintensities region recognizing system according to an embodiment of the present disclosure.

FIG. 5 is a schematic diagram showing a magnetic resonance imaging white matter hyperintensities region recognizing system 500 according to an embodiment of the present disclosure. The white matter hyperintensities region recognizing system 500 includes an input device 540, a storage device 550, and a processor 560. The input device 540 may be a transmission port (USB, GPIB or another interface). The storage device 550 may be a read only memory (ROM), a flash memory, a floppy disk, a hard disk, an optical disk, a pen drive, a magnetic tape, a network accessible database, or any other suitable non-transitory computer-readable medium with the same function. The processor 560 may be a central processing unit (CPU), a microprocessor or another circuit.

The input device 540 receives a FLAIR MRI image 510, a T1 weighted MRI image 520 and a diffusion weighted MRI image 530 as sources for image processing. The storage device 550, which is coupled to the input device 540, stores the FLAIR MRI image 510, the T1 weighted MRI image 520 and the diffusion weighted MRI image 530 for subsequent image processing.

Although the FLAIR MRI image 510, the T1 weighted MRI image 520 and the diffusion weighted MRI image 530 are usually measured when a target object is immobilized, some external factors (e.g., head movement of the target object) which cause slight movement of the image are still difficult to avoid. Therefore, the processor 560 registers the images. With respect to the FLAIR MRI image 510, the processor 560 adjusts locations of the T1 weighted MRI image and locations of the diffusion weighted MRI image so that voxels of the three images have a location corresponding to the relation of brain structure for subsequent image processing. After the image registration, a registered T1 weighted MRI image and a registered diffusion weighted MRI image are formed.

If the target object has WMH in a FLAIR image, the voxel intensity of the same location is lower in a T1 weighted MRI image so that this is often mistaken to be gray matter. Therefore, the processor 560 compensates the registered T1 weighted MRI image $V_{registered\ T1w}$ by the FLAIR image $V_{FLAIR}$, and fuses the two image to form a fused image by the following equation of voxel intensity:

$$V_{fusion} = kV_{registered\ T1w} + (1-k)V_{FLAIR}$$

Where k is a constant and its range is [0, 1]. In the present embodiment, k is set as 0.8 and the fused image can be used to distinguish gray matter regions from white matter regions. The processor 560 then determines a white matter mask through the fused image to emphasize the white matter regions in the image.

In order to exclude regions except for white matter regions to execute a WMH region analysis process, the processor 560 forms an intersection image by taking an intersection of the aforementioned white matter mask and the FLAIR MRI image. In other words, the processor 560 multiplies intensity values of voxels in the white matter mask and location-corresponding intensity values of voxels in the FLAIR MRI image together. The product shows that intensity values of the voxels in the other regions are all zeros except for the white matter region so that the other regions displayed black, and the white matter region remains in the FLAIR MRI image. Because the voxel intensity distributed range of every FLAIR MRI image pending for analysis is not necessarily the same, the processor 560 performs an intensity value normalization process of the voxels in the intersection image so that ranges of the values are all adjusted to [0, 100] for appliance of WMH determining conditions before the WMH region is determined. Next, the processor 560 inspects the intensity values of voxels in turn, and if an intensity value of a voxel is larger than a voxel intensity threshold value, then the processor 560 selects the voxel as belonging to a first region indicating that it may be a WMH region. In the present embodiment, the voxel intensity threshold value is set as 65, and if an intensity value of a voxel is larger than 65, then the voxel is selected as belonging to a first region indicating that it may be a WMH region. The voxel intensity threshold value also can be flexibly designed according to actual requirements.

Because the voxel intensity of a cerebral infarct region is close to the voxel intensity of a WMH region in a FLAIR MRI image 510, the cerebral infarct region is usually selected as belonging to the first region. As shown in FIG. 3A, a WMH region 302, a cerebral infarct region and a surrounding region thereof are all selected as belonging to the first region, and the aforementioned registered diffusion weighted MRI image is used to distinguish the three regions. The cerebral infarct region is distinctive in the registered diffusion weighted MRI image, and therefore the processor 560 can mark the cerebral infarct region through the registered diffusion weighted MRI image to form a second region 306. When a continuous area 304 of the first region overlaps the second region 306, the second region 306 is removed from the continuous area 304 to form a remaining region 308 (FIG. 3C), in which the cerebral infarct region and the surrounding region thereof that overlaps the second region 306 are the aforementioned continuous area 304. In addition, a surrounding edema phenomenon often accompanies the cerebral infarct region and may lie in a circular region that is peripheral to the second region 306 and not included in the second region 306 so that the edema region is not removed when the processor 560 removes the second region 306 from the continuous area 304. The processor 560 takes a voxel number ratio of the second region to the continuous area as a condition of determining the edema region. When the continuous area 304 overlaps the second region 306 and a voxel number ratio of the second region 306 to the continuous area 304 is larger than a predetermined value, then the processor 560 determines the remaining region 308 as a peri-infarct edema of cerebral infarct and removes the remaining region 308 (step S116). The remaining region 308 is reserved if it does not satisfy the condition. Specifically, the predetermined value is 80%, the continuous area 304 that overlaps the second region 306 is the cerebral infarct region and the surrounding region thereof, and when a voxel intensity ratio of the second region 306 to the continuous area 304 is larger than 80%, then the processor 560 removes the remaining region to form a FLAIR MRI image with only the WMH region 302 marked (FIG. 3D). If there is at least one continuous area 304 that overlaps the second region 306, an independent determination is made as to whether at least one remaining region 308 after removing the second region 306 is to be removed or reserved by each voxel number ratio. The present disclosure not only removes the cerebral infarct region with similar voxel intensity, but also has a mechanism of removing the surrounding region of the cerebral infarct region so that an image with the WMH region is generated after the two filtering steps through the present embodiment of the present disclosure.

However, voxel intensity of a junction region of cerebral gray matter and white matter is also close to voxel intensity of a WMH region in a FLAIR MRI image so that the processor 560 may select the junction region as belonging to the first region, and therefore the junction region of cerebral gray matter and white matter must be removed from the first region. In one embodiment, the processor 560 determines a junction region of cerebral gray matter and white matter from the fused image. If an intensity value of a voxel is between $(I_{average,\ GM}+0.5I_{stdev,\ GM})$ and $(I_{average,\ WM}-0.5I_{stdev,\ WM})$, then the processor 560 determines the voxel as the junction region 401 of cerebral gray matter and white matter, as shown as mesh region in FIG. 4A, where $I_{average,\ GM}$ is an average value of voxel intensity in the gray matter region, $I_{stdev,\ GM}$ is a standard deviation of voxel intensity in the gray matter region, $I_{average,\ WM}$ is an average value of voxel intensity in the white matter region, and $I_{stdev,\ WM}$ is a standard deviation of voxel intensity in the white matter region. Before removing the second region, the processor 560 removes the junction region 401 from the first region. This is realized by performing a method involving the processor 560 determining that a central voxel is junction-connected if a central voxel or any of the eight neighboring voxels thereof in the first region overlaps the aforementioned junction region 401 of cerebral gray matter and white matter. As shown in FIG. 4B, if over 80% of voxels in a continuous area are junction-connected, then the processor 560 determines the continuous area to be junction-connected and removes the continuous area from the first region to exclude the junction regions 402, 404 of cerebral gray matter and white matter and reserve the first region 406 without the junction region of cerebral gray matter and white matter.

In order to generate a white matter mask suitable for a target object, in one embodiment, the processor 560 determines a set of transformation parameters through DARTEL, in which the set of transformation parameters is used for mutual deformation of an ICBM template image and the fused image of the target object. The processor 560 separately selects a white matter image and a gray matter image from the ICBM template image, and also separately selects a white matter image and a gray matter image from the fused image. The processor 560 analyzes the four images to generate the set of transformation parameters through a DARTEL module embedded in SPM8 software. By using the set of transformation parameters, template images are inputted and the processor 560 outputs images of a target object that anatomically correspond to the template images after a deformation process.

In one embodiment, the processor 560 executes a binarization process of a template white matter image to form a template white matter mask, in which intensity values of voxels are all in the range of [0, 1] and a condition of the binarization process is set such that when an intensity value of a voxel is larger than 0.5, the processor 560 determines the voxel as the white matter region and the intensity value of the voxel is designated as one. If an intensity value of a voxel is smaller than 0.5, the processor 560 designates the intensity value of the voxel as zero and therefore forms the template white matter mask. The processor 560 then deforms the template white matter mask into an initial white matter mask of the target object, in which the initial white matter mask anatomically corresponds to the template white matter mask through the aforementioned set of transformation parameters generated by DARTEL.

However, because the voxel intensity of a corpus callosum region of the brain is close to the voxel intensity of a white matter region in a FLAIR MRI image 510, intensity values of voxels in the corpus callosum region are also designated as one in the aforementioned binarization process, and therefore, the corpus callosum region must be removed from the initial white matter mask to form a white matter mask without the corpus callosum region. In one embodiment, the processor 560 determines a template corpus callosum mask from the ICBM template image, and deforms the template corpus callosum mask into a corpus callosum mask of the target object through the aforementioned set of transformation parameters generated by DARTEL. In one embodiment, the processor 560 executes an intersection process of the initial white matter mask and the corpus callosum mask. In other words, the processor 560 multiplies the intensity values of the voxels in the two masks that are located correspondingly together to form the white matter mask without the corpus callosum region. In an alternative embodiment, the processor 560 forms the aforementioned corpus callosum mask by manually determining a corpus callosum region and designating intensity values of the voxels in the corpus callosum region as zeros.

Since some of the steps are optional in the MRI white matter hyperintensities region recognizing method 100. In one embodiment, MRI white matter hyperintensities region recognizing method can be executed as follows. First, a FLAIR MRI image, a T1 weighted MRI image and a diffusion weighted MRI image are received as sources for image processing. The FLAIR MRI image, the T1 weighted MRI image and the diffusion weighted MRI image are stored for subsequent image processing. Although the FLAIR MRI image, the T1 weighted MRI image and the diffusion weighted MRI image are usually measured when a target object is immobilized, some external factors (e.g., head movement of the target object) that cause slight movement of the image are still difficult to avoid. With respect to the FLAIR MRI image, locations of the spin-lattice relaxation time weighted MRI image are registered so that voxels of the two images have a location corresponding to the relation of brain structure for the subsequent image processing and a registered T1 weighted MRI image is formed. A first region is determined through the fluid attenuation inversion recovery (FLAIR) MRI image and the registered spin-lattice relaxation time weighted MRI image, where the first region indicating may be a white matter hyperintensities (WMH) region. Because the voxel intensity of a cerebral infarct region is close to the voxel intensity of a WMH region in a FLAIR MRI image, the cerebral infarct region is usually selected as belonging to the first region. With respect to the FLAIR MRI image, locations of the diffusion weighted MRI image are registered so that voxels of the two images have a location corresponding to the relation of brain structure for the subsequent image processing and a registered diffusion weighted MRI image is formed. A cerebral infarct region and a surrounding region thereof are all selected as belonging to the first region, and the aforementioned registered diffusion weighted MRI image is used to distinguish the three regions. The cerebral infarct region is distinctive in the registered diffusion weighted MRI image, and therefore the cerebral infarct region can be marked through the registered diffusion weighted MRI image to form a second region. When a continuous area of the first region overlaps the second region, removing the second region from the continuous area to form a remaining region. In one embodiment, when the continuous area overlaps the second region and a voxel number ratio of the second region to the continuous region is larger than a predetermined value, then the remaining region is determined as a peri-infarct edema of cerebral infarct and the remaining region is removed. However, those skilled in the art should understand that the sequence of the steps in the present embodiment can be adjusted according to actual needs, unless such a sequence is specified. All or some of the steps can even be executed simultaneously. Accordingly, in one embodiment, an MRI white matter hyperintensities region recognizing system with the same hardware as the MRI white matter hyperintensities region recognizing system 500 can execute the aforementioned embodiment of MRI white matter hyperintensities region recognizing method.

In conclusion, the present disclosure can remove a cerebral infarct region with the assistance of a diffusion weighted MRI image and reserve a WMH region of a FLAIR MRI image by determining whether a remaining region is peri-infarct edema through the aforementioned embodiments. Moreover, the WMH region is automatically detected to eliminate the burden associated with manual recognition, build a consistent standard, and improve the recognizing efficiency.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A magnetic resonance imaging white matter hyperintensities region recognizing method, comprising:
    (a) receiving and storing a fluid attenuation inversion recovery (FLAIR) MRI image, a spin-lattice relaxation time weighted MRI image and a diffusion weighted MRI image; with respect to the fluid attenuation inversion recovery (FLAIR) MRI image, registering the spin-lattice relaxation time weighted MRI image to form a registered spin-lattice relaxation time weighted MRI image; determining a first region through the fluid attenuation inversion recovery (FLAIR) MRI image and the registered spin-lattice relaxation time weighted MRI image;
    (b) with respect to the fluid attenuation inversion recovery (FLAIR) MRI image, registering the diffusion weighted MRI image to form a registered diffusion weighted MRI image; determining a second region through the registered diffusion weighted MRI image;
    (c) when a continuous area of the first region overlaps the second region, removing the second region from the continuous area to form a remaining region; and
    (d) when the continuous area overlaps the second region and a ratio of the second region to the continuous area is larger than a predetermined value, removing the remaining region.

2. The magnetic resonance imaging white matter hyperintensities region recognizing method of claim 1, further comprising:
    fusing the fluid attenuation inversion recovery (FLAIR) MRI image and the registered spin-lattice relaxation time weighted MRI image to form a fused image and determining the white matter mask through the fused image;
    determining a junction region of cerebral gray matter and white matter from the fused image; and
    before removing the second region, removing the junction region from the first region.

3. The magnetic resonance imaging white matter hyperintensities region recognizing method of claim 1, further comprising:
    taking an intersection image of the fluid attenuation inversion recovery (FLAIR) MRI image and a white matter mask;
    normalizing the intersection image; and
    after the normalization, when an intensity value of a voxel in the intersection image is larger than a voxel intensity threshold value, the voxel is selected as belonging to a first region.

4. The magnetic resonance imaging white matter hyperintensities region recognizing method of claim 3, further comprising:
    fusing the fluid attenuation inversion recovery (FLAIR) MRI image and the registered spin-lattice relaxation time weighted MRI image to form a fused image, and determining the white matter mask through the fused image;
    determining a set of transformation parameters from the fused image and a known template brain image by diffeomorphic anatomical registration through exponentiated Lie algebra (DARTEL), wherein the set of transformation parameters is used for mutual deformation of the fused image and the known template brain image.

5. The magnetic resonance imaging white matter hyperintensities region recognizing method of claim 4, further comprising:
   executing a binarization process of a known template white matter image to form a template white matter mask; and
   executing a deformation process of the template white matter mask through the set of transformation parameters to form an initial white matter mask.

6. The magnetic resonance imaging white matter hyperintensities region recognizing method of claim 5, further comprising:
   determining a template corpus callosum mask from the known template brain image;
   executing a deformation process of the template corpus callosum mask through the set of transformation parameters to form a corpus callosum mask; and
   executing an intersection process of the initial white matter mask and the corpus callosum mask to form the white matter mask.

7. A magnetic resonance imaging white matter hyperintensities region recognizing system, comprising:
   an input device configured to receive a fluid attenuation inversion recovery (FLAIR) MRI image, a spin-lattice relaxation time weighted MRI image and a diffusion weighted MRI Image;
   a storage device configured to store the fluid attenuation inversion recovery (FLAIR) MRI image, the spin-lattice relaxation time weighted MRI image and the diffusion weighted MRI image; and
   a processor coupled to the storage device and configured to execute the following steps:
   (a) with respect to the fluid attenuation inversion recovery (FLAIR) MRI image, registering the spin-lattice relaxation time weighted MRI image to form a registered spin-lattice relaxation time weighted MRI image; determining a first region through the fluid attenuation inversion recovery (FLAIR) MRI image and the registered spin-lattice relaxation time weighted MRI image;
   (b) with respect to the fluid attenuation inversion recovery (FLAIR) MRI image, registering the diffusion weighted MRI image to form a registered diffusion weighted MRI image; determining a second region through the registered diffusion weighted MRI image;
   (c) when a continuous area of the first region overlaps the second region, removing the second region from the continuous area to form a remaining region; and
   (d) when the continuous area overlaps the second region and a ratio of the second region to the continuous area is larger than a predetermined value, removing the remaining region.

8. The magnetic resonance imaging white matter hyperintensities region recognizing system of claim 7, wherein the processor fuses the fluid attenuation inversion recovery (FLAIR) MRI image and the registered spin-lattice relaxation time weighted MRI image to form a fused image, determines a junction region of cerebral gray matter and white matter from the fused image, and removes the junction region from the first region before removing the second region.

9. The magnetic resonance imaging white matter hyperintensities region recognizing system of claim 7, wherein the processor takes an intersection image of the fluid attenuation inversion recovery (FLAIR) MRI image and a white matter mask and normalizes the intersection image, and after the normalization, when an intensity value of a voxel in the intersection image is larger than a voxel intensity threshold value, the processor selects the voxel as belonging to a first region.

10. The magnetic resonance imaging white matter hyperintensities region recognizing system of claim 9, wherein the processor fuses the fluid attenuation inversion recovery (FLAIR) MRI image and the registered spin-lattice relaxation time weighted MRI image to form a fused image, determines the white matter mask through the fused image, and determines a set of transformation parameters from the fused image and a known template brain image by diffeomorphic anatomical registration through exponentiated Lie algebra (DARTEL), wherein the set of transformation parameters is used for mutual deformation of the fused image and the known template brain image.

11. The magnetic resonance imaging white matter hyperintensities region recognizing system of claim 10, wherein the processor executes a binarization process of a known template white matter image to form a template white matter mask, and executes a deformation process of the template white matter mask through the set of transformation parameters to form an initial white matter mask.

12. The magnetic resonance imaging white matter hyperintensities region recognizing system of claim 11, wherein the processor determines a template corpus callosum mask from the known template brain image, executes a deformation process of the template corpus callosum mask through the set of transformation parameters to form a corpus callosum mask, and executes an intersection process of the initial white matter mask and the corpus callosum mask to form the white matter mask.

* * * * *